United States Patent
Saito et al.

(10) Patent No.: US 9,541,487 B2
(45) Date of Patent: Jan. 10, 2017

(54) METHOD OF MANAGING DECONTAMINATION AND DECONTAMINATION MANAGEMENT APPARATUS FOR USE IN THE METHOD

(75) Inventors: Masanobu Saito, Ibaraki (JP); Keisuke Kodera, Hachioji (JP); Masatoyo Oshiro, Hirakata (JP)

(73) Assignee: Taikisha Ltd., Tokyo (JP)

( * ) Notice: Subject to any disclaimer, the term of this patent is extended or adjusted under 35 U.S.C. 154(b) by 1133 days.

(21) Appl. No.: 13/574,477

(22) PCT Filed: May 18, 2011

(86) PCT No.: PCT/JP2011/061386
§ 371 (c)(1),
(2), (4) Date: Oct. 5, 2012

(87) PCT Pub. No.: WO2011/148833
PCT Pub. Date: Dec. 1, 2011

(65) Prior Publication Data
US 2013/0204549 A1  Aug. 8, 2013

(30) Foreign Application Priority Data
May 24, 2010  (JP) ................. 2010-118533

(51) Int. Cl.
*A61L 2/24* (2006.01)
*G01F 22/00* (2006.01)
*G01N 7/14* (2006.01)
*A61L 2/20* (2006.01)

(52) U.S. Cl.
CPC ............... *G01N 7/14* (2013.01); *A61L 2/208* (2013.01); *A61L 2202/14* (2013.01)

(58) Field of Classification Search
CPC ........ A61L 2/202; A61L 2202/14; G01N 7/14
USPC .................................................. 422/3; 702/50
See application file for complete search history.

(56) References Cited

U.S. PATENT DOCUMENTS

| | | | |
|---|---|---|---|
| 5,173,258 A | 12/1992 | Childers | |
| 7,025,932 B2 | 4/2006 | Martin et al. | |
| 7,186,371 B1 | 3/2007 | Watling | |
| 8,071,021 B2 | 12/2011 | Hill | |

FOREIGN PATENT DOCUMENTS

| | | |
|---|---|---|
| JP | 2003501149 A | 1/2003 |
| JP | 2003527211 A | 9/2003 |
| JP | 2005143725 A | 6/2005 |
| JP | 2006288527 A | 10/2006 |
| JP | 2009535215 A | 10/2009 |
| WO | 2007130852 A2 | 11/2007 |

OTHER PUBLICATIONS

Ohe, The vapor-liquid equilibrium, Tokyo University of Science, 2012, pp. 1-6, available at http://www.joryu.jp/index.htm.

*Primary Examiner* — Kevin Joyner
(74) *Attorney, Agent, or Firm* — The Webb Law Firm

(57) ABSTRACT

It is determined that indoor condensation of hydrogen peroxide vapor is to occur, if there is a solution with which both (Equation 1): $PT \cdot y1 = P01 \cdot x1 \cdot \gamma 1$ and (Equation 2): $PT \cdot y2 = P02 \cdot x2 \cdot \gamma 2$ hold. With this, it is possible to accurately determine whether indoor condensation of hydrogen peroxide vapor is to occur or not in decontamination.

7 Claims, 3 Drawing Sheets

METHOD OF MANAGING DECONTAMINATION AND DECONTAMINATION MANAGEMENT APPARATUS FOR USE IN THE METHOD

TECHNICAL FIELD

The present invention relates to a method of managing decontamination for use in decontaminating the interior of a decontamination target room by supplying an amount of hydrogen peroxide vapor thereto. The invention relates also to a decontamination management apparatus for use in the decontamination management method.

BACKGROUND ART

As decontamination using hydrogen peroxide vapor, there are a wet type decontamination (wet method) in which hydrogen peroxide vapor supplied to a decontamination target room is caused to be condensed inside the room and a dry type decontamination (dry method) in which hydrogen peroxide vapor supplied to a decontamination target room is allowed to exist as it is in the form of vapor phase without being condensed.

And, with the wet type decontamination as compared with the dry type decontamination, high decontamination effect can be achieved even in a shorter period. On the other hand, the wet type decontamination can not be used in a situation where the condensate of hydrogen peroxide vapor gives an adverse effect to indoor substance, such as causing chemical or physical alternation thereof.

Conversely, the dry type decontamination method provides only lower decontamination effect than the wet type. And, because of this, the former requires a longer decontamination period, but provides the advantage of giving less adverse effect to indoor substance.

Regarding such decontamination using hydrogen peroxide vapor as above, Patent Document 1 (in particular, claim 1 and paragraphs 0066 through 0067) discloses a dry type decontamination method comprising monitoring indoor condensation of hydrogen peroxide vapor by a condensation sensor, specifying, based on monitoring information, the concentration of the hydrogen peroxide indoors when indoor condensation of hydrogen peroxide vapor has vanished and decontaminating the indoor under the specified concentration condition (Prior Art 1).

Further, this Patent Document 1 (in particular, paragraph 0009) discloses another dry type decontamination method comprising specifying a desired concentration of the hydrogen peroxide present indoors in a range where no indoor condensation of hydrogen peroxide vapor will occur, in the course of progressively increasing the indoor hydrogen peroxide concentration and decontaminating the room interior under this specified concentration condition (Prior Art 2).

On the other hand, Patent Document 2 (in particular, paragraph 0067) discloses a wet type decontamination method comprising monitoring indoor condensation amount of hydrogen peroxide vapor by a condensation sensor and adjusting the amount of hydrogen peroxide vapor to be supplied to the room interior based on the monitoring information (Prior Art 3).

PRIOR ART DOCUMENTS

Patent Documents

Patent Document 1: Japanese Unexamined Patent Application Publication No. 2006-288527

Patent Document 2: Japanese Unexamined Patent Application Publication No. 2005-143725

SUMMARY OF THE INVENTION

Object to be Achieved by Invention

However, with the dry type decontamination arrangements according to Prior Art 1 and Prior Art 2 described above, despite the indoor hydrogen peroxide concentration being maintained at a specified concentration, indoor condensation of hydrogen peroxide vapor may be invited inadvertently due to e.g. temperature/humidity condition of the room interior. So, the adaptability of the method to condition changes is poor.

Further, in the case of the arrangement as provided in Prior Art 1 wherein condensation of hydrogen peroxide vapor is monitored by a condensation sensor, condensation occurring at a local point in the room interior may be overlooked; hence, accurate monitoring of the entire room interior is difficult and a monitoring error tends to occur. And, due to this, an error may occur also in the specification of the concentration, so that inadvertent indoor condensation may occur.

On the other hand, with the wet type decontamination according to Prior Art 3, while the supply amount of hydrogen peroxide vapor is adjusted based on the monitoring information of the condensation sensor, with the monitoring of the condensation condition with such condensation sensor, accurate monitoring of the entire room interior is difficult and a monitoring error tends to occur. Due to this, an error may occur in the adjustment amount of the supplying amount of the hydrogen peroxide vapor, which may inadvertently invite a no-condensation condition where condensation of hydrogen peroxide vapor is non-existent inside the room.

Moreover, in the case of decontamination using hydrogen peroxide vapor, self decomposition of the hydrogen peroxide vapor can easily occur, so that due to water component generated as a result of this self decomposition, the indoor humidity too will be changed accordingly. So, the above-described problem tends to occur even more easily.

In view of the above-described state of the art, the principal object of the present invention is to achieve reasonable determination of whether indoor condensation of hydrogen peroxide vapor is to occur or not, thus making it possible to obtain, in an accurate and reliable manner, a desired decontamination condition, either with the dry type decontamination or with the wet type decontamination.

Means for Achieving the Object

The first characterizing feature of the present invention relates to a decontamination management method, which is characterized in that:

based on indoor temperature/humidity and indoor hydrogen peroxide concentration in a decontamination target room;

a condition setting step is effected for obtaining a hydrogen peroxide vapor pressure (PT·y1) and a water vapor pressure (PT·y2) at that indoor temperature/humidity in the decontamination target room and obtaining also a saturated hydrogen peroxide vapor pressure (P01) when the hydrogen peroxide component alone exists at that indoor temperature and a saturated water vapor pressure (P02) when the water component alone exists at that indoor temperature;

a computing step is effected for solving: (Equation 1) and (Equation 2):

$$PT \cdot y1 = P01 \cdot x1 \cdot \gamma1 \quad \text{(Equation 1)},$$

$$PT \cdot y2 = P02 \cdot x2 \cdot \gamma2 \quad \text{(Equation 2)}$$

in which the respective vapor pressures ($PT \cdot y1$) and ($PT \cdot y2$) and the respective saturated vapor pressures ($P01$) and ($P02$) obtained by the condition setting step are to be substituted respectively, under a condition specified by (Equation 3):

$$x1 + x2 = 1 \quad \text{(Equation 3)},$$

in accordance with a correlation between a liquid phase mol fraction ($x1$) and an activity coefficient ($\gamma1$) for the hydrogen peroxide component and a correlation between a liquid phase mol fraction ($x2$) and an activity coefficient ($\gamma2$) for the water component, with sequentially varying the value of the liquid phase mol fraction ($x1$) for the hydrogen peroxide component from 0 to 1 and sequentially varying also the activity coefficient ($\gamma1$) for the hydrogen peroxide component as well as the liquid phase mol fraction ($x2$) and the activity coefficient ($\gamma2$) for the water component in accordance with said sequential varying of ($x1$); and a determining step is effected for determining that condensation of the hydrogen peroxide vapor is to occur inside the decontamination target room if there exists a solution with which both said (Equation 1) and (Equation 2) hold or determining that condensation of the hydrogen peroxide vapor is not to occur if there does not exist a solution with which both said (Equation 1) and (Equation 2) hold.

Namely, simultaneous holding of the above Equation 1 and Equation 2 (ref: http://www.joryu.jp/index.htm "What is a vapor-liquid equilibrium?") each representing a vapor-liquid equilibrium means that for the indoor temperature/humidity and indoor hydrogen peroxide concentration that together constitute the condition at the time of their simultaneous holding of the equations, the vapor-liquid equilibrium (i.e. a condition where the vapor phase and the liquid phase co-exist in the room interior as shown in FIG. 3) represented by the established Equation 1 and Equation 2 is to occur.

Therefore, with the decontamination management method according to the above-described first characterizing feature, at the computing step, Equation 1 and Equation 2 are computed with sequentially and hypothetically varying the liquid phase mol fraction ($x1$) and the activity coefficient ($\gamma1$) for the hydrogen peroxide component and also the liquid phase mol fraction ($x2$) and the activity coefficient ($\gamma2$) for the water component, respectively. And, in this process, if there is found a condition of presence of a solution with which both Equation 1 and Equation 2 hold, it is then determined that condensation of the hydrogen peroxide vapor (i.e. a liquid phase) is to occur inside the decontamination target room. Also, if there is not found a condition of presence of a solution with which both Equation 1 and Equation 2 hold, it is determined that condensation of the hydrogen peroxide vapor (i.e. a liquid phase) is not to occur inside the decontamination target room.

That is, with this management method, in comparison with the above-described condensation monitoring arrangement using a condensation sensor which often suffers a monitoring error, only with specifying the indoor temperature/humidity and indoor hydrogen peroxide concentration, determination of whether indoor condensation of hydrogen peroxide vapor is to occur or not can be made in an accurate and stable manner for the whole room interior.

Therefore, if the indoor temperature/humidity and the indoor hydrogen peroxide concentration are adjusted based on the result of the above determination, in the case of the dry type decontamination, the inadvertent occurrence of indoor condensation of hydrogen peroxide vapor can be avoided reliably, so that the favorable dry type decontamination can be implemented in an accurate and stable manner. Further, in the case of the wet type decontamination, the inadvertent occurrence of the no-condensation condition of condensation of hydrogen peroxide vapor becoming non-existent in the room can be avoided reliably, so that the favorable wet type decontamination can be implemented in an accurate and stable manner.

Incidentally, the decontamination management method according to the first characterizing feature can be used in any desired manner that allows expectation of the above-described desirable effect, such as a simulation type mode of use wherein an optimum indoor temperature/humidity and an optimum indoor hydrogen peroxide concentration to be used in an actual decontamination operation are decided based on the results of respective cases of varying in many ways the conditions of the indoor temperature/humidity and indoor hydrogen peroxide concentration as the subject conditions by way of hypothesis, computation, etc or an operational mode of use wherein the indoor temperature/humidity and indoor hydrogen peroxide concentration are adjusted sequentially in realtime, based on the results of determination using, as the conditions, measured values of the indoor temperature/humidity and indoor hydrogen peroxide concentration in an actual decontamination operation.

Also, for the correlation between a liquid phase mol fraction ($x1$) and an activity coefficient ($\gamma1$) for the hydrogen peroxide component and the correlation between a liquid phase mol fraction ($x2$) and an activity coefficient ($\gamma2$) for the water component, reference can be made to existing data (see FIG. 5) disclosed in various documents. (source of FIG. 5: http://www.h2o2.com/technical-library/physical-chemical-properties/physical-properties/default.aspx?pid=27&name=Activity-Coefficients).

Further, in implementing the first characterizing feature arrangement, instead of the computation of (Equation 1) and (Equation 2) with sequentially varying the value of the liquid phase mol fraction ($x1$) for the hydrogen peroxide component from 0 to 1 under the condition of (Equation 3) and sequentially varying also the activity coefficient ($\gamma1$) for the hydrogen peroxide component as well as the liquid phase mol fraction ($x2$) and the activity coefficient ($\gamma2$) for the water component in accordance with said sequential varying of ($x1$), as a substantially identical computation, the computation of (Equation 1) and (Equation 2) can be made with sequentially varying the value of the liquid phase mode fraction ($x2$) for the water component from 0 to 1 under the condition of (Equation 3) and sequentially varying also the activity coefficient ($\gamma2$) for the water component as well as the liquid phase mol fraction ($x1$) and the activity coefficient ($\gamma1$) for the hydrogen peroxide component in accordance with said sequential varying of ($x2$). This arrangement can be made for the computation step in the sixth characterizing feature and the seventh characterizing feature to be described later, The second characterizing feature of the present invention relates to a decontamination management method, which is characterized in that:

an amount of hydrogen peroxide vapor generated from hydrogen peroxide solution by a decontaminating gas generating means is combined with an amount of carrier air having a predetermined temperature/humidity and fed together through a decontaminating gas feed passage to the decontamination target room, and the indoor humidity is computed with using a computation model including, as parameters thereof, an amount of water vapor formed of water component contained in the hydrogen peroxide solution which is generated in association with the generation of the hydrogen peroxide vapor from the hydrogen peroxide solution by the decontaminating gas generating means and an amount of water vapor generated due to self-decomposition immediately after the generation of the hydrogen peroxide vapor by the decontaminating gas generating means.

That is, when hydrogen peroxide vapor is generated from hydrogen peroxide solution, there is generated also water vapor constituted from the water component contained in the hydrogen peroxide solution as the source material and this generated water vapor, together with the generated hydrogen peroxide vapor, is combined with the carrier air and fed together to the decontamination target room, so that the water vapor may cause an alteration in the indoor humidity of the decontamination target room.

Also, the self-decomposition of hydrogen peroxide vapor into water and oxygen occurs immediately after the generation of hydrogen peroxide vapor and an amount of water vapor generated in association with this self-decomposition is also combined with the carrier air and fed together to the decontamination target room, so that this water vapor also may cause an alteration in the indoor humidity of the decontamination target room.

Therefore, according to the second characterizing feature which provides computation of indoor humidity with using the above-described computation model, the indoor humidity can be computed accurately with taking into consideration also the influence from the water vapor constituted from the water content in the hydrogen peroxide solution as the source material as well as the influence from the water vapor generated in association with self decomposition immediately after the generation of hydrogen peroxide vapor. In correspondence therewith, the accuracy of the determination of the indoor condensation consisting of the above-described condition setting step, the computing step and the determining step can be enhanced even further.

Incidentally, in implementing the second characterizing feature arrangement, as to the indoor temperature and the indoor hydrogen peroxide concentration respectively, any one of a hypothetical value, a computed value and a measured value can be used.

The third characterizing feature of the present invention relates to a decontamination management method, characterized in that:

in parallel with the feeding of hydrogen peroxide vapor to the decontamination target room, the indoor condensation determination comprised of the condition setting step, the computing step and the determining step is effected in repetition by a set micro period.

That is, with this arrangement, for possible sequential alternation of indoor temperature/humidity or indoor hydrogen peroxide concentration which can occur in the course of feeding of hydrogen peroxide vapor to the decontamination target room, it is possible to determine at each timing therein whether indoor condensation of hydrogen peroxide vapor is to occur or not. With this, it becomes possible to avoid in an even more reliable manner the inadvertent occurrence of indoor condensation of hydrogen peroxide vapor in the dry type decontamination or the inadvertent occurrence of non-condensation of hydrogen peroxide vapor in the wet type decontamination.

The fourth characterizing feature of the present invention relates to a decontamination management method, characterized in that:

in computing the indoor humidity for each cycle of the indoor condensation determination, the indoor humidity is computed with using a computation model including, as a parameter thereof, an amount of water vapor generated due to over-time self decomposition of hydrogen peroxide vapor in the decontamination target room.

That is, the hydrogen peroxide vapor fed to the decontamination target room is self-decomposed into water and oxygen with lapse of time, so that the water vapor resulting from this over-time self decomposition may cause an alteration in the indoor humidity of the decontamination target room.

Therefore, according to the fourth characterizing feature which provides computation of indoor humidity with using the above-described computation model for each cycle of indoor condensation determination at the set small time interval, the indoor humidity can be computed accurately with taking into consideration also the influence from the water vapor generated due to over-time self decomposition of hydrogen peroxide vapor in the decontamination target room. In correspondence therewith, the accuracy of the determination of the indoor condensation for each cycle can be enhanced even further.

Incidentally, in implementing the fourth characterizing feature arrangement, as to the indoor temperature and the indoor hydrogen peroxide concentration respectively for each cycle of indoor condensation determination, any one of a hypothetical value, a computed value and a measured value can be used.

The fifth characterizing feature of the present invention relates to a decontamination management method, characterized in that:

if it is determined at the determining step that condensation of hydrogen peroxide vapor is to occur, at least one of an indoor hydrogen peroxide concentration, an indoor hydrogen peroxide solution concentration, an indoor hydrogen peroxide solution amount and an indoor solution film thickness of the decontamination target room after the condensation is computed with using the substituted values used when both the (Equation 1) and (Equation 2) held.

That is, with this fifth characterizing feature, the indoor decontamination condition of the decontamination target room can be determined in an even more elaborate manner especially in the case of the wet type decontamination. If the indoor temperature/humidity or indoor hydrogen peroxide concentration is adjusted based on the result of such elaborate determination, the desired decontaminated condition can be obtained in an even more reliable and stable manner.

The sixth characterizing feature of the present invention relates to a decontamination management method, characterized in that:

an amount of hydrogen peroxide vapor generated from hydrogen peroxide solution by a decontaminating gas generating means is combined with an amount of carrier air having a predetermined temperature/humidity and fed together through a decontaminating gas feed passage to the decontamination target room;

based on an in-passage temperature/humidity and an in-passage hydrogen peroxide concentration of the decontaminating gas feed passage, a condition setting step is effected for obtaining a hydrogen peroxide vapor pressure (PT'·y1') and a water vapor pressure (PT'·y2') at that in-passage temperature/humidity in the decontaminating gas feed passage, and obtaining also a saturated hydrogen peroxide vapor pressure (P01') when the hydrogen peroxide component alone exists at that in-passage temperature and a saturated water vapor pressure (P02') when the water component alone exists at that in-passage temperature;

a computing step is effected for solving: (Equation 1') and (Equation 2'):

$$PT' \cdot y1' = P01' \cdot x1 \cdot \gamma1 \quad \text{(Equation 1')},$$

$$PT' \cdot y2' = P02' \cdot x2 \cdot \gamma2 \quad \text{(Equation 2')}$$

in which the respective vapor pressures (PT'·y1') and (PT'·y2') and the respective saturated vapor pressures (P01') and (P02') obtained by the condition setting step for the gas passage are to be substituted respectively, under a condition specified by (Equation 3'):

$$x1 + x2 = 1 \quad \text{(Equation 3')},$$

in accordance with a correlation between a liquid phase mol fraction (x1) and an activity coefficient (γ1) for the hydrogen peroxide component and a correlation between a liquid phase mol fraction (x2) and an activity coefficient (γ2) for the water component, with sequentially varying the value of the liquid phase mol fraction (x1) for the hydrogen peroxide component from 0 to 1 and sequentially varying also the activity coefficient (γ1) for the hydrogen peroxide component as well as the liquid phase mol fraction (x2) and the activity coefficient (γ2) for the water component in accordance with said sequential varying of (x1); and a determining step is effected for determining that condensation of the hydrogen peroxide vapor is to occur inside the decontaminating gas feed passage if there exists a solution with which both said (Equation 1') and (Equation 2') hold or determining that condensation of the hydrogen peroxide vapor is not to occur inside the decontaminating gas feed passage if there does not exist a solution with which both said (Equation 1') and (Equation 2') hold.

Namely, depending on the condition, condensation of hydrogen peroxide vapor may occur inside the decontaminating gas feed passage to which hydrogen peroxide vapor generated by the decontaminating gas generating means is fed as being carried by the carrier gas. However such in-passage condensation is not needed generally in either the dry type decontamination or the wet type decontamination, and such in-passage condensation can cause an alternation in the indoor humidity or indoor hydrogen peroxide concentration in the decontamination target room.

In view of the above, according to the sixth characterizing feature arrangement, in a manner similar to the indoor condensation determination provided in the first characterizing feature for determining whether condensation of hydrogen peroxide vapor is to occur in the decontamination target room or not, it is possible to determine accurately whether condensation of hydrogen peroxide vapor is to occur or not inside the decontaminating gas feed passage.

Therefore, if the in-passage temperature/humidity or the in-passage hydrogen peroxide concentration of the decontaminating gas feed passage is adjusted based on the result of this determination, in-passage condensation of hydrogen peroxide vapor inside the decontaminating gas feed passage can be avoided in a reliable manner, thereby to prevent alternation in the indoor humidity or indoor hydrogen peroxide concentration of the decontamination target room due to occurrence of such in-passage condensation. As a result in correspondence with this, a desired indoor decontaminated condition can be obtained in an even more reliable and stable manner in both the dry type decontamination and the wet type decontamination.

The seventh characterizing feature of the present invention relates to a decontamination management method, characterized by:

based on indoor temperature/humidity and indoor hydrogen peroxide concentration in a decontamination target room a condition setting step for object surface is effected for obtaining a hydrogen peroxide vapor pressure (PT·y1) and a water vapor pressure (PT·y2) at that indoor temperature/humidity in the decontamination target room, and obtaining also a saturated hydrogen peroxide vapor pressure (P01") when the hydrogen peroxide component alone exists at a surface temperature of an indoor object present in the decontamination target room and a saturated water vapor pressure (P02") when the water component alone exists at a surface temperature of an indoor object present in the decontamination target room;

a computing step for object surface is effected for solving: (Equation 1") and (Equation 2"):

$$PT \cdot y1 = P01'' \cdot x1 \cdot \gamma1 \quad \text{(Equation 1'')},$$

$$PT \cdot y2 = P02'' \cdot x2 \cdot \gamma2 \quad \text{(Equation 2'')}$$

in which the respective vapor pressures (PT·y1) and (PT·y2) and the respective saturated vapor pressures (P01") and (P02") obtained by the condition setting step for object surface are to be substituted respectively, under a condition specified by (Equation 3"):

$$x1 + x2 = 1 \quad \text{(Equation 3'')},$$

in accordance with a correlation between a liquid phase mol fraction (x1) and an activity coefficient (γ1) for the hydrogen peroxide component and a correlation between a liquid phase mol fraction (x2) and an activity coefficient (γ2) for the water component, with sequentially varying the value of the liquid phase mol fraction (x1) for the hydrogen peroxide component from 0 to 1 and sequentially varying also the activity coefficient (γ1) for the hydrogen peroxide component as well as the liquid phase mol fraction (x2) and the activity coefficient (γ2) for the water component in accordance with said sequential varying of (x1); and a determining step for object surface is effected for determining that condensation of the hydrogen peroxide vapor is to occur on the surface of the indoor object in the decontamination target room if there exists a solution with which both said (Equation 1") and (Equation 2") hold or determining that condensation of the hydrogen peroxide vapor is not to occur on the surface of the indoor object in the decontamination target room if there does not exist a solution with which both said (Equation 1") and (Equation 2") hold.

Namely, depending on the surface temperature of an object (including a room wall, a ceiling or floor) present inside the decontamination target room, condensation of hydrogen peroxide vapor can occur locally on the surface of this object or non-condensation of hydrogen peroxide vapor can occur locally and only on the surface of the object.

In view of the above, according to the seventh characterizing feature arrangement described above, in a manner similar to the indoor condensation determination provided in the first characterizing feature for determining whether condensation of hydrogen peroxide vapor is to occur inside the decontamination target room or not, it is possible to determine accurately whether condensation of hydrogen peroxide vapor is to occur or not on the surface of an indoor object as a determination target.

Therefore, if the indoor temperature/humidity or indoor hydrogen peroxide concentration or even the surface temperature of the indoor object, if possible, is adjusted based on the result of this determination, in the case of the dry type decontamination, local occurrence of hydrogen peroxide vapor condensation on the surface of the indoor object can be avoided reliably. Also, in the case of the wet type decontamination, local occurrence of non-condensation of hydrogen peroxide vapor limited on the indoor object can be avoided reliably. With these, in either the dry type decontamination or the wet type decontamination, a desired indoor decontaminated condition can be obtained in an even more reliable and stable manner.

Incidentally, in a manner similar to the implementation of any one of the second through fifth characterizing feature when effecting the indoor condensation determination according to the first characterizing feature, when the gas passage condensation determination according to the sixth characterizing feature or the object surface condensation determination according to the seventh characterizing feature is to be implemented, this should be implemented together with an arrangement corresponding to any one of the second through fifth characterizing feature, if needed.

Namely, in the gas passage condensation determination according to the sixth characterizing feature or the object surface condensation determination according to the seventh characterizing feature, an amount of hydrogen peroxide vapor generated from hydrogen peroxide solution by a decontaminating gas generating means is combined with an amount of carrier air having a predetermined temperature/humidity and fed together through a decontaminating gas feed passage to the decontamination target room, and the in-passage humidity of the decontaminating gas feed passage or the indoor humidity of the decontamination target room may be computed with using a computation model including, as parameters thereof, an amount of water vapor formed of water component contained in the hydrogen peroxide solution which is generated in association with the generation of the hydrogen peroxide vapor from the hydrogen peroxide solution by the decontaminating gas generating means and an amount of water vapor generated due to self-decomposition immediately after the generation of the hydrogen peroxide vapor by the decontaminating gas generating means.

Also, in parallel with the feeding of hydrogen peroxide vapor to the decontamination target room, the condensation, determination for gas passage or object surface comprised of the condition setting step, the computing step and the determining step may be effected in repetition by a set micro period.

Further, in the above case, in computing the indoor humidity for each cycle of the condensation determination for the object surface condensation determination, the indoor humidity may be computed with using a computation model including, as a parameter thereof, an amount of water vapor generated due to overtime self decomposition of hydrogen peroxide vapor in the decontamination target room.

Further, if it is determined at the determining step for gas passage or object surface that condensation of hydrogen peroxide vapor is to occur, at least one of hydrogen peroxide concentration in the gas passage or on the object surface after condensation, a hydrogen peroxide solution concentration in the gas passage or on the object surface after condensation, and a solution film thickness in the gas passage or on the object surface after condensation may be computed with using the substituted values used when both the (Equation 1') and (Equation 2') or both the (Equation 1") and (Equation 2") held.

In the respective equations described above, PT represents a gas phase total pressure in the decontamination target room, y1 represents a gas phase mol fraction for hydrogen peroxide component in the decontamination target room, y2 represents a gas phase mol fraction for water component in the decontamination target room, PT' represents a gas phase total pressure in the decontaminating gas feed passage, y1' represents a gas phase mol fraction for hydrogen peroxide component in the decontaminating gas feed passage, y2' represents a gas phase mol fraction for water component in the decontaminating gas feed passage.

The eighth characterizing feature of the present invention relates to a decontamination management apparatus characterized by:

an automatic determining means for automatically effecting said condition setting step, said computing step and said determining step and then outputting the result obtained by the determining step.

That is, with the decontamination management apparatus according to this eighth characterizing feature, with the automatic effecting of the respective steps and outputting the result by the automatic determining means, indoor condensation determination by the decontamination management method according to the first characterizing feature can be carried out easily and speedily.

Incidentally, in implementing the decontamination management apparatus according to the eighth characterizing feature, if necessary, the apparatus may be configured to effect also the decontamination management method according to the second through seventh characterizing features.

MODES OF EMBODYING THE INVENTION

Figure 1:
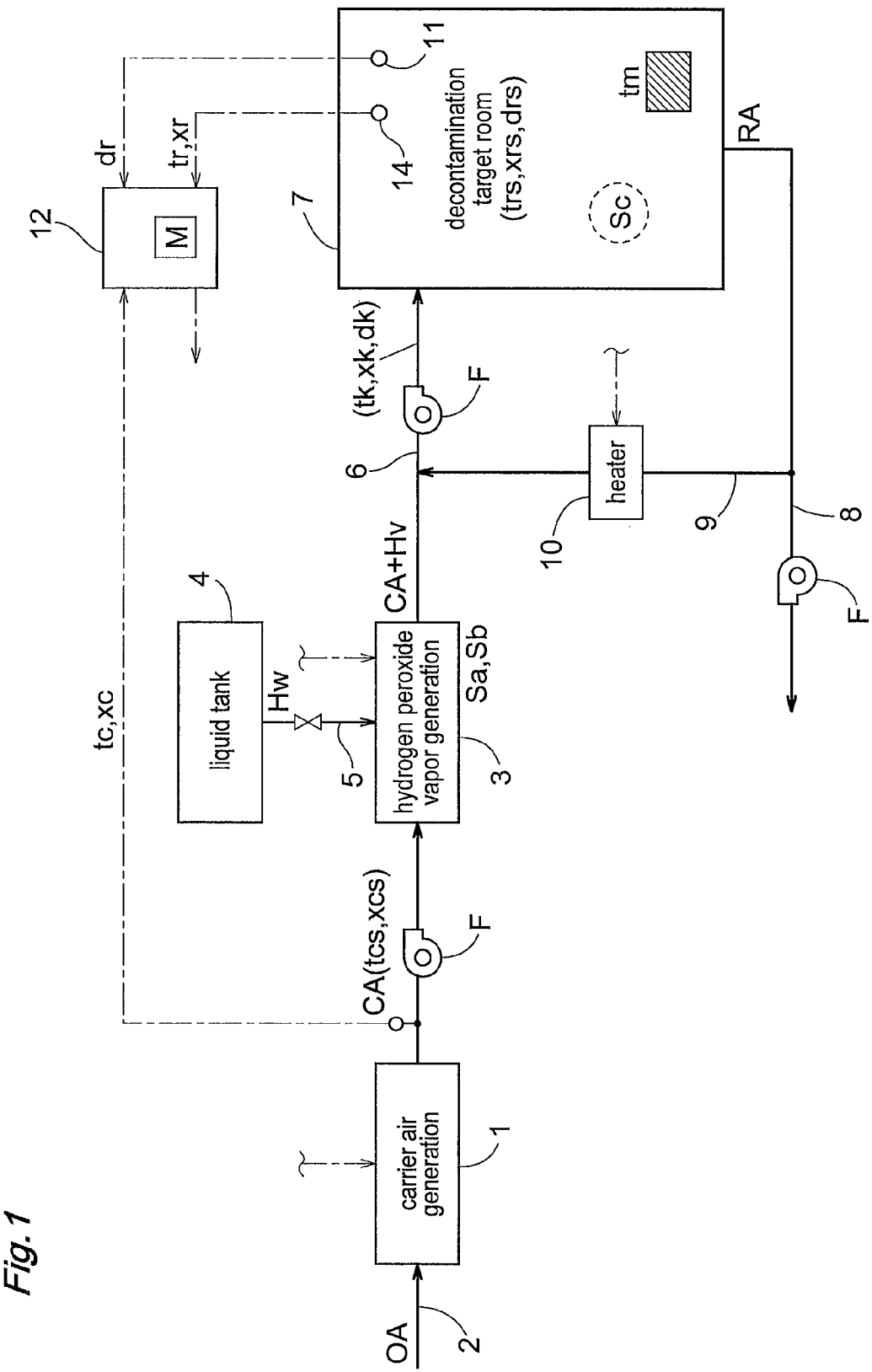
FIG. 1 is a system construction diagram of a decontamination system.

FIG. 1 shows a decontamination system. In FIG. 1, numeral 1 denotes an air conditioner for generating carrier air, configured to effect temperature/humidity adjustment on ambient air OA introduced through a ambient air introducing passage 2 thereby to generate carrier air CA having set temperature/humidity (temperature: tcs, humidity: xcs).

Numeral 3 denotes a hydrogen peroxide vapor generator configured as a decontaminating gas generating means for evaporating an amount of hydrogen peroxide solution fed from a liquid tank 4 through a liquid feed passage 5 thereby to generate hydrogen peroxide vapor Hv.

Namely, with this decontamination system in operation, the hydrogen peroxide vapor Hv generated by the hydrogen peroxide vapor generator 3 is combined with the carrier air CA having the set temperature/humidity (temperature: tcs, humidity: xcs) and fed together through a decontaminating gas passage 6 into a decontamination target room 7, thereby to decontaminate the interior of this decontamination target room 7.

Numeral 8 denotes a gas exhaust passage configured to exhaust an amount of indoor (room) air RA equal to the amount of ambient air introduced from the ambient air introducing passage 2 from the decontamination target room 7 to the outside. Also, numeral 9 denotes a circulation passage for circulating the indoor air RA of the decontamination target room 7. This circulation passage 9 incorporates a heater 10 for heating the air RA present inside the room.

Next, a decontamination operation will be explained, mainly for the dry type decontamination wherein hydrogen peroxide vapor Hv is not to be condensed in the decontamination target room 7.

Figure 2:
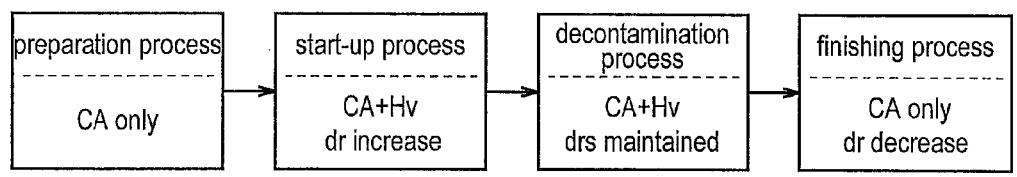
FIG. 2 is a process diagram illustrating flow of respective steps in a decontamination operation.

As shown in FIG. 2, a decontamination operation for decontaminating the inside of the decontamination target room 7 with feeding of the hydrogen peroxide vapor Hv consists essentially of a preparation process, a start-up process, a decontamination process and a finishing process. In the preparation process, after completion of a normal air conditioning operation for the decontamination target room 7, first, an amount of the carrier air CA having the set temperature/humidity (temperature: tcs, humidity: xcs) is fed through the decontaminating gas feed passage 6 into the decontamination target room 7, without generating hydrogen peroxide vapor Hv yet.

That is, with feeding of this carrier air CA alone, the indoor temperature/humidity (temperature: tr, humidity: xr) of the decontamination target room 7 is adjusted to the set indoor temperature/humidity (temperature: trs, humidity: xrs) which is suitable for decontamination and the inside of the decontaminating gas passage 6 is adjusted to a temperature at which no condensation of hydrogen peroxide vapor Hv occurs.

Incidentally, if needed in this preparation process, in parallel with the feeding of the carrier air CA, a portion of the indoor air RA of the decontamination target room 7 is caused to be circulated through the circulation passage 9 under operation of the heater 10.

In the start-up process subsequent to the preparation process, a great amount of hydrogen peroxide vapor Hv is generated in the hydrogen peroxide vapor generator 3 and this generated hydrogen peroxide vapor Hv is combined with the carrier air CA, so that the resultant carrier air CA with increased hydrogen peroxide concentration is fed to the decontamination target room 7 so as to speedily raise the indoor hydrogen peroxide concentration (dr) of the decontamination target room 7 to a set indoor hydrogen peroxide concentration (drs) for decontamination under the above-described set indoor temperature/humidity condition (trs, xrs).

In the decontamination process subsequent to the start-up process, the generation amount Gv of the hydrogen peroxide vapor Hv by the hydrogen peroxide vapor generator 3 is adjusted to more decreasing side than the start-up process, and the generation amount Gv of the hydrogen peroxide vapor Hv by the hydrogen peroxide vapor generator 3 is adjusted through adjustment of the feeding amount of the hydrogen peroxide solution Hw to the hydrogen peroxide vapor generator 3, based on the detected indoor hydrogen peroxide concentration (dr) obtained by a concentration sensor 11 so that the indoor hydrogen peroxide concentration (dr) of the decontamination target room 7 may be maintained to the decontamination set indoor hydrogen peroxide concentration (drs) enhanced in the start-up process, for a predetermined decontamination period T.

As the predetermined decontamination period T, a period required for complete killing of bacteria with the decontamination set indoor hydrogen peroxide concentration (drs) is obtained by e.g. an experiment or the like and then a period with an addition thereto of a certain ratio of safety is set as this predetermined decontamination period T.

Upon lapse of the predetermined decontamination period T, the decontamination process is shifted to the finishing process. And, in this finishing process, with completion of the generation of hydrogen peroxide vapor Hv by the hydrogen peroxide vapor generator 3, carrier air CA having returning set temperature/humidity (tsc', xcs') is fed and the indoor air RA of the decontamination target room 7 containing the hydrogen peroxide vapor Hv is discharged to the outside through the gas exhaust passage 8. With this, the hydrogen peroxide concentration (dr) of the decontamination target room 7 is reduced to a limit concentration (e.g. 1 ppm) harmless to humans and also the indoor temperature/humidity (tr, xr) of the decontamination target room 7 is returned to the normal indoor temperature/humidity (trs', xrs').

Numeral 12 denotes a decontamination operation controller for automatically effecting the decontamination operation consisting of the above-described processes. This decontamination operation controller 12 automatically controls the carrier air feeding air conditioner 1, the hydrogen peroxide vapor generator 3, the heater 10 and fans F incorporated in respective air passages, in accordance with a decontamination operation program, based on detection information of a carrier air temperature/humidity sensor 13 for detecting the temperature/humidity (tc, xc) of the carrier air CA, a decontamination target room temperature/humidity sensor 14 for detecting the temperature/humidity (tr, xr) of the decontamination target room 7, the concentration sensor 11, etc.

Further, this decontamination operation controller 12 is provided with a function as an automatic determining means for automatically determining e.g. a decontaminated condition of the decontamination target room 7 in a simulation. Then, based on the result of this determination, the set temperature/humidity (tcs, xcs) of the carrier air CA, the set indoor temperature/humidity (trs, xrs) of the decontamination target room 7, etc. in the decontamination operation program are determined.

Specifically, as this automatic determination function, the decontamination operation controller 12 is configured to automatically effect the following processes (a) through (d).

(a) For each of the start-up process and the decontamination process in which the hydrogen peroxide vapor Hv is fed to the decontamination target room 7, at each timing for a set small unit period $\Delta T$, the indoor temperature/humidity (tr, xr) and the indoor hydrogen peroxide concentration (dr) of the decontamination target room 7 as well as the in-passage temperature/humidity (tk, rk) and the in-passage hydrogen peroxide concentration (dk) of the decontaminating gas feed passage 6 at each timing are computed in a virtual manner, with using a computation model M.

The computation model M employed in the above computation uses, as parameters thereof, the set temperature/humidity (tcs, xcs) of the carrier air CA, the blow amount Q of the carrier air CA, the generation amount Gv of hydrogen peroxide vapor Hv in the hydrogen peroxide vapor generator 3, a generation amount Gsa of water vapor Sa constituted from water content in the hydrogen peroxide solution. Hw generated in association with the generation of hydrogen peroxide vapor Hv in the hydrogen peroxide vapor generator 3, a generation amount Gsb of water vapor Sb generated due to self-decomposition immediately after the generation of the hydrogen peroxide vapor Hv in the hydrogen peroxide vapor generator 3, a generation amount Gsc of water vapor Sc generated due to over-time self decomposition of the hydrogen peroxide vapor Hv in the decontamination target room 7, the initial temperature/humidity (tra, xra) of the decontamination target room 7, the room capacity V of the decontamination target room 7, and computes the indoor temperature/humidity (tr, xr), the indoor hydrogen peroxide concentration (dr), the in-passage hydrogen peroxide temperature/humidity (tk, rk), and the in-passage hydrogen peroxide concentration (dk).

Namely, this computation model M is configured to effect the humidity computation, with taking into consideration, the water vapor Sa constituted from water content in the hydrogen peroxide solution Hw generated in association with the generation of hydrogen peroxide vapor Hv in the hydrogen peroxide vapor generator 3, the water vapor Sb generated due to self-decomposition immediately after the generation of the hydrogen peroxide vapor Hv in the hydrogen peroxide vapor generator 3, and the water vapor Sc generated due to over-time self decomposition of the hydrogen peroxide vapor Hv in the decontamination target room 7.

Incidentally, this computation is effected in a virtual manner for obtaining any change in the indoor temperature/humidity (tr, xr) and the indoor hydrogen peroxide concentration (dr) for each set micro period $\Delta T$ in response to the feeding of the carrier air CA containing the hydrogen peroxide vapor Hv and water vapors Sa, Sb to the decontamination target room 7, on the assumption of no occurrence of condensation of hydrogen peroxide vapor Hv, in each of the start-up process and the decontamination process.

Figure 3:
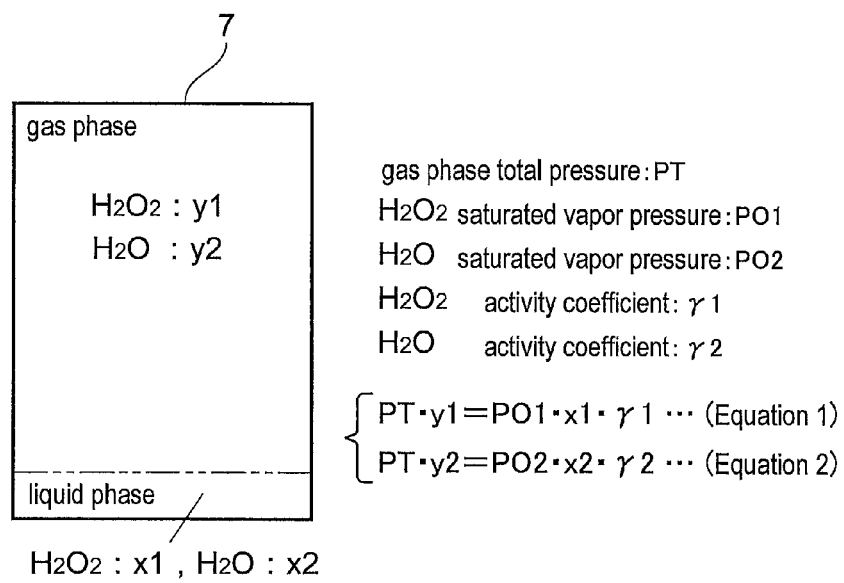
FIG. 3 is a diagram showing an indoor condition of a decontamination target room.
Figure 4:
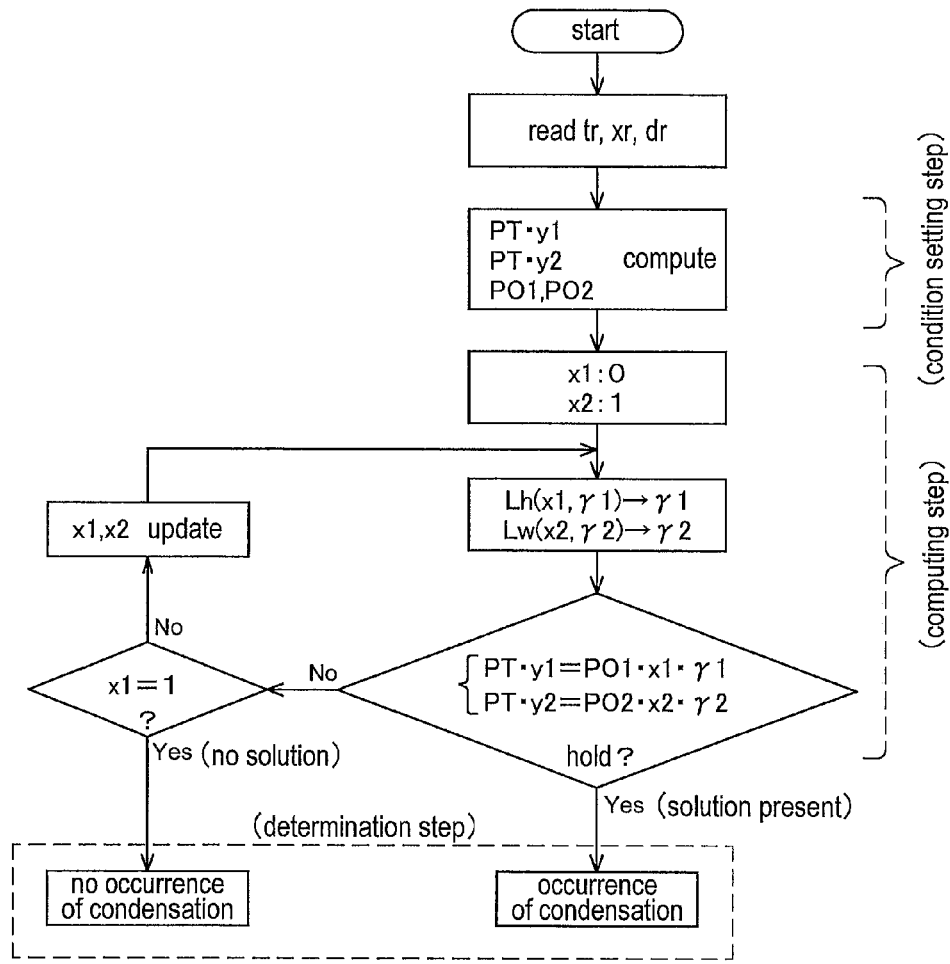
FIG. 4 is a flowchart illustrating flow of condensation determination.

(b) In each of the start-up process and the decontamination process, for each set micro period $\Delta T$, indoor condensation determination is effected in repetition for determining whether condensation of hydrogen peroxide vapor Hv inside the decontamination target room 7 is to occur or not (see FIG. 3 and FIG. 4).

In each cycle of indoor condensation determination, based on the indoor temperature/humidity (tr, xr) and the indoor hydrogen peroxide concentration (dr) in the decontamination target room 7 computed with using the computation model M, there is effected a condition setting step for obtaining a hydrogen peroxide vapor pressure (PT·y1) and a water vapor pressure (PT·y2) at that indoor temperature/humidity (tr, xr) in the decontamination target room 7 and obtaining also a saturated hydrogen peroxide vapor pressure (P01) when the hydrogen peroxide component alone exists at that indoor temperature (tr) and a saturated water vapor pressure (P02) when the water component alone exists at that indoor temperature (tr).

Figure 5:
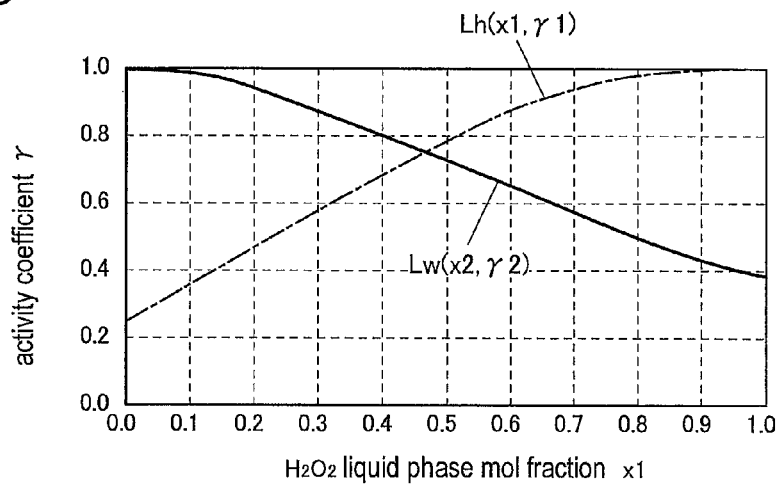
FIG. 5 is a graph illustrating correlation between a liquid phase mol concentration and an activity coefficient.

Then, there is effected a computing step for solving: (Equation 1) and (Equation 2):

$$PT \cdot y1 = P01 \cdot x1 \cdot \gamma 1 \quad \text{(Equation 1)},$$

$$PT \cdot y2 = P02 \cdot x2 \cdot \gamma 2 \quad \text{(Equation 2)}$$

in which the respective vapor pressures (PT·y1) and (PT·y2) and the respective saturated vapor pressures (P01) and (P02) obtained by the condition setting step are to be substituted respectively, under a condition specified by (Equation 3):

$$x1 + x2 = 1 \quad \text{(Equation 3)},$$

in accordance with a correlation (Lh) between a liquid phase mol fraction (x1) and an activity coefficient ($\gamma 1$) for the hydrogen peroxide component and a correlation (Lw) between a liquid phase mol fraction (x2) and an activity coefficient ($\gamma 2$) for the water component as shown in FIG. 5, with sequentially varying the value of the liquid phase mol fraction (x1) for the hydrogen peroxide component from 0 to 1 and sequentially varying also the activity coefficient ($\gamma 1$) for the hydrogen peroxide component as well as the liquid phase mol fraction (x2) and the activity coefficient ($\gamma 2$) for the water component in accordance with said sequential varying of (x1).

Then, as a determining step, it is determined that condensation of the hydrogen peroxide vapor Hv is to occur inside the decontamination target room 7 if there exists a solution with which both said (Equation 1) and (Equation 2) hold or determined that condensation of the hydrogen peroxide vapor Hv is not to occur inside the decontamination target room 7 if there does not exist a solution with which both said (Equation 1) and (Equation 2) hold.

If it is determined at the determining step that condensation of hydrogen peroxide vapor (Hv) is to occur inside the decontamination target room 7, an indoor hydrogen peroxide concentration (dr), an indoor hydrogen peroxide solution concentration, an indoor hydrogen peroxide solution amount and an indoor solution film thickness of the decontamination target room after the condensation is (are) computed and recorded with using the substituted values used when both the (Equation 1) and (Equation 2) held.

(c) In each one of the start-up process and the decontamination process, for each set micro period $\Delta T$, there is effected in repetition determination whether condensation of hydrogen peroxide vapor Hv is to occur or not inside the decontaminating gas feed passage 6.

In the gas passage condensation determination for each cycle, based on an in-passage temperature/humidity (tk, xk) and an in-passage hydrogen peroxide concentration (dk) of the decontaminating gas feed passage 6 computed with using the computation model M, there is effected a condition setting step for obtaining a hydrogen peroxide vapor pressure (PT'·y1') and a water vapor pressure (PT'·y2') at that in-passage temperature/humidity (tk, xk) in the decontaminating gas feed passage 6 and obtaining also a saturated hydrogen peroxide vapor pressure (P01') when the hydrogen peroxide component alone exists at that in-passage temperature (tk) and a saturated water vapor pressure (P02') when the water component alone exists at that in-passage temperature (tk).

Subsequently, there is effected a computing step for solving: (Equation 1') and (Equation 2'):

$$PT' \cdot y1' = P01' \cdot x1 \cdot \gamma 1 \quad \text{(Equation 1')},$$

$$PT' \cdot y2' = P02' \cdot x2 \cdot \gamma 2 \quad \text{(Equation 2')}$$

in which the respective vapor pressures (PT'·y1') and (PT'·y2') and the respective saturated vapor pressures (P01') and (P02') obtained by the condition setting step for the gas passage are to be substituted respectively, under a condition specified by (Equation 3'):

$$x1 + x2 = 1 \quad \text{(Equation 3')},$$

in accordance with a correlation (Lh) between a liquid phase mol fraction (x1) and an activity coefficient (γ1) for the hydrogen peroxide component and a correlation (Lw) between a liquid phase mol fraction (x2) and an activity coefficient (γ2) for the water component as shown in FIG. 5, and with sequentially varying the value of the liquid phase mol fraction (x1) for the hydrogen peroxide component from 0 to 1 and sequentially varying also the activity coefficient (γ1) for the hydrogen peroxide component as well as the liquid phase mol fraction (x2) and the activity coefficient (γ2) for the water component in accordance with said sequential varying of (x1).

Then, as a determining step for gas passage, it is determined that condensation of the hydrogen peroxide vapor Hv is to occur inside the decontaminating gas feed passage 6 if there exists a solution with which both said (Equation 1') and (Equation 2') hold or determining that condensation of the hydrogen peroxide vapor Hv is not to occur inside the decontaminating gas feed passage 6 if there does not exist a solution with which both said (Equation 1') and (Equation 2') hold.

If it is determined at the gas passage determining step that condensation of hydrogen peroxide vapor Hv is to occur inside the decontaminating gas feed passage 6, an in-passage hydrogen peroxide concentration (dk), an in-passage hydrogen peroxide solution concentration, an in-passage hydrogen peroxide solution amount and an in-passage solution film thickness of the decontaminating gas feed passage 6 after the condensation is (are) computed and recorded with using the substituted values used when both the (Equation 1') and (Equation 2') held.

(d) In each one of the start-up process and decontamination process, for each set micro period ΔT, there is effected in repetition determination whether condensation of hydrogen peroxide vapor Hv is to occur or not on the surface of an indoor object present in the decontamination target room 7.

In the object surface condensation determination for each cycle, based on the indoor temperature/humidity (tr, xr) and the indoor hydrogen peroxide concentration (dr) computed at each timing with using the computation model M, there is effected a condition setting step for obtaining a hydrogen peroxide vapor pressure (PT·y1) and a water vapor pressure (PT·y2) at that indoor temperature/humidity (tr, xr) in the decontaminating target room 7 and obtaining also a saturated hydrogen peroxide vapor pressure (P01") when the hydrogen peroxide component alone exists at the surface temperature (tm) of the determination target indoor object in the determination target room 7 and a saturated water vapor pressure (P02") when the water component alone exists at the surface temperature (tm) of the determination target indoor object in the determination target room 7.

Then, there is effected a computing step for solving: (Equation 1") and (Equation 2"):

$$PT \cdot y1 = P01'' \cdot x1 \cdot \gamma 1 \quad \text{(Equation 1''),}$$

$$PT \cdot y2 = P02'' \cdot x2 \cdot \gamma 2 \quad \text{(Equation 2'')}$$

in which the respective vapor pressures (PT·y1) and (PT·y2) and the respective saturated vapor pressures (P01") and (P02") obtained by the object surface condition setting step are to be substituted respectively, under a condition specified by (Equation 3"):

$$x1 + x2 = 1 \quad \text{(Equation 3''),}$$

in accordance with a correlation (Lh) between a liquid phase mol fraction (x1) and an activity coefficient (γ1) for the hydrogen peroxide component and a correlation (Lw) between a liquid phase mol fraction (x2) and an activity coefficient (γ2) for the water component as shown in FIG. 5, and with sequentially varying the value of the liquid phase mol fraction (x1) for the hydrogen peroxide component from 0 to 1 and sequentially varying also the activity coefficient (γ1) for the hydrogen peroxide component as well as the liquid phase mol fraction (x2) and the activity coefficient (γ2) for the water component in accordance with said sequential varying of (x1).

Then, as a determining step for object surface, it is determined that condensation of the hydrogen peroxide vapor Hv is to occur on the surface of the determination target indoor object in the determination target room 7 if there exists a solution with which both said (Equation 1") and (Equation 2") hold or determining that condensation of the hydrogen peroxide vapor Hv is not to occur if there does not exist a solution with which both said (Equation 1") and (Equation 2") hold.

If it is determined at the object surface determining step that condensation of hydrogen peroxide vapor Hv is to occur on the surface of the determination target indoor object in the determination target room 7, a hydrogen peroxide concentration (dr), a hydrogen peroxide solution concentration, a hydrogen peroxide solution amount and a solution film thickness on the indoor object surface after the condensation is (are) computed and recorded with using the substituted values used when both the (Equation 1") and (Equation 2") held.

With repeated executions of the decontamination condition determination consisting of the above steps (a) through (d) with varying the operation conditions such as the temperature/humidity (tc, xc) of the carrier air CA, the generation amount Gv of the hydrogen peroxide vapor Hv, etc., in the case of the dry type decontamination in which the hydrogen peroxide vapor Hv is not to be condensed inside the decontamination target room 7, there will be specified an optimum dry decontamination condition with which it is determined that no condensation of hydrogen peroxide vapor Hv is to occur in all of (b) the indoor condensation determination, (c) the gas passage condensation determination and (d) the object surface condensation determination and that allows obtaining of a desired indoor hydrogen peroxide concentration (dr).

And, the temperature/humidity (tc, xc) of the carrier air CA, the indoor temperature/humidity (tr, xr) and the indoor hydrogen peroxide concentration (dr) of the decontamination target room 7 when such optimum dry decontamination condition as above was obtained from the decontamination condition evaluation consisting of the above steps (a) through (d) will be employed as the set temperature/humidity (tcs, xcs) of the carrier air CA, the set indoor temperature/humidity (trs, xrs) and the set indoor hydrogen peroxide concentration (drs) of the decontamination target room 7 in the decontamination operation program.

Next, there will be described the case of the wet type decontamination in which hydrogen peroxide vapor Hv is caused to be condensed inside the decontamination target room 7.

There will be specified the optimum wet decontamination condition with which (c) the gas passage condensation determination determines non occurrence of in-passage condensation of hydrogen peroxide vapor Hv, (b) the indoor condensation determination and (d) the object surface condensation determination both determine occurrence of condensation of hydrogen peroxide vapor Hv and with which the indoor hydrogen peroxide concentration (dr) after condensation, the hydrogen peroxide concentration of the solution after condensation and the liquid film thickness can be as desired.

And, like the above-described case of the dry type decontamination, the temperature/humidity (tc, xc) of the carrier air CA, the indoor temperature/humidity (tr, xr) and the indoor hydrogen peroxide concentration (dr) (after condensation) of the decontamination target room 7 when such optimum wet decontamination condition as above was obtained from the decontamination condition evaluation consisting of the above steps (a) through (d) will be employed as the set temperature/humidity (tcs, xcs) of the carrier air CA, the set indoor temperature/humidity (trs, xrs) and the set indoor hydrogen peroxide concentration (drs) of the decontamination target room 7 in the decontamination operation program.

That is, with determinations of the respective set values based on the result of simulation of the decontamination operation as described above, in the above-described automatic decontamination operation by the decontamination operation controller 12, in the case of the dry type decontamination, favorable dry type decontamination will be implemented in a reliable and stable manner with effectively avoiding inadvertent occurrence of indoor condensation of hydrogen peroxide vapor Hv; whereas, in the case of the wet type decontamination, favorable wet type decontamination will be implemented in a reliable and stable manner with effectively avoiding occurrence of non-condensation condition with absence of indoor condensation of hydrogen peroxide vapor Hv.

Other Embodiments

Next, other embodiments of the present invention will be described one by one.

In the foregoing embodiment, there was described an example wherein the decontamination operation controller 12 for automatically effecting a decontamination operation is provided with the function as the automatic determining means for automatically determining e.g. the decontaminated condition of the decontamination target room 7 by simulation of the decontamination operation. Instead, this automatic determining function may be provided to a dedicated management apparatus separate from the decontamination operation controller 12.

Further, in the foregoing embodiment, there was described an exemplary arrangement wherein in the simulation of decontamination operation, there is effected a decontamination condition determination consisting of the processes of (a) through (d) and based on the result of this determination, the set temperature/humidity (tcs, xcs) of the carrier air CA, the set indoor temperature/humidity (trs, xrs) and the set indoor hydrogen oxide concentration (drs) of the decontamination target room 7 are selected and specified. Instead of this or in addition to this arrangement, the indoor temperature/humidity (tr, xr), the indoor hydrogen peroxide concentration (dr), the in-passage temperature/humidity (tk, tx), the in-passage hydrogen peroxide concentration (dk), and the surface temperature (tm) of indoor object, etc. may be measured in parallel with an actual decontamination operation, and for this measured value, (b) the indoor condensation determination, (c) the gas passage condensation determination and (d) the object surface condensation determination, may be effected. Then, based on the results of these determinations, the temperature/humidity (tc, xc) of the carrier air CA, the indoor temperature/humidity (tr, xr) or the indoor hydrogen peroxide concentration (dr) of the decontamination target room 7 may be adjusted sequentially in realtime.

In the foregoing embodiment, at the computing step, the computing step for gas passage, the computing step for object surface, (Equation 1), (Equation 2), (Equation 1'), (Equation 2'), (Equation 1''), (Equation 2'') are computed, with sequentially varying the value of the liquid phase mol fraction (x1) for the hydrogen peroxide component from 0 to 1 and sequentially varying also the activity coefficient ($\gamma 1$) for the hydrogen peroxide component as well as the liquid phase mol fraction (x2) and the activity coefficient ($\gamma 2$) for the water component in accordance with said sequential varying of (x1). Instead, as a substantially equivalent computation, it is possible to sequentially varying the value of the liquid phase mol fraction (x2) for the water component from 0 to 1 and sequentially varying also the activity coefficient ($\gamma 2$) for the water component as well as the liquid phase mol fraction (x1) and the activity coefficient ($\gamma 1$) for the hydrogen peroxide component in accordance with said sequential varying of (x2).

Further, in the above, generally, higher determination accuracy can be obtained when the change amount per cycle for the liquid phase mol fraction (x1) for the hydrogen peroxide component or the liquid phase mol fraction (x2) for the water component is smaller. In this regard, an appropriate amount can be selected, taking into consideration the computation load, etc.

The decontamination target room 7 can be a room for manufacturing pharmaceutical products or a room provided for any other purpose, as long as it is a room requiring indoor decontamination.

INDUSTRIAL APPLICABILITY

The present invention is applicable to decontamination which is to be implemented for indoor space for various purposes in various fields.

DESCRIPTION OF REFERENCE MARKS/NUMERALS 7 decontamination target room
tr indoor temperature
xr indoor humidity
dr indoor hydrogen peroxide concentration
PT·y1 indoor hydrogen peroxide vapor pressure
PT·y2 indoor water vapor pressure
P01 saturated hydrogen peroxide vapor pressure at indoor temperature
P02 saturated water vapor pressure at indoor temperature
x1 liquid phase mol fraction of hydrogen peroxide component
$\gamma 1$ activity coefficient of hydrogen peroxide component
x2 liquid phase mol fraction of water component
$\gamma 1$ activity coefficient of water component
Lh correlation
Lw correlation
3 decontaminating gas generating means
Hw hydrogen peroxide solution
Hv hydrogen peroxide vapor
CA carrier air
tcs temperature of carrier air
xcs humidity of carrier air
6 decontaminating gas feed passage
Sa water vapor
Gsa generation amount Sb water vapor
Gsb generation amount
Sc water vapor
Gsc generation amount
M computation model
ΔT set micro period
tk in-passage temperature
tx in-passage humidity
dk in-passage hydrogen peroxide concentration
PT'·y1' in-passage hydrogen peroxide vapor pressure
PT'·y2' in-passage water vapor pressure
P01' saturated hydrogen peroxide vapor pressure at in-passage temperature
P02' saturated water vapor pressure at in-passage temperature
tm surface temperature
P01" saturated hydrogen peroxide vapor pressure at surface temperature
P02" saturated water vapor pressure at surface temperature
12 automatic determining means

The invention claimed is:

1. A decontamination management method, comprising:
   a) determining the hydrogen peroxide vapor pressure (PT·y1) and water vapor pressure (PT·y2) in a decontamination target room using the indoor temperature and humidity of the decontamination target room and a specified concentration of hydrogen peroxide;
   b) determining a saturated hydrogen peroxide vapor pressure (P01), if a hydrogen peroxide component existed alone at the indoor temperature of the decontamination target room;
   c) determining a saturated water vapor pressure (P02) if the water component existed alone at the indoor temperature of the decontamination target room;
   d) solving (Equation 1) and (Equation 2), using the vapor pressures, (PT·y1) and (PT·y2), and the saturated vapor pressures, (P01) and (P02), obtained in steps (a) through (c)

$$PT \cdot y1 = P01 \cdot x1 \cdot \gamma1 \quad \text{(Equation 1)},$$

$$PT \cdot y2 = P02 \cdot x2 \cdot \gamma2 \quad \text{(Equation 2)},$$

wherein x1 is equal to a liquid phase mol fraction of hydrogen peroxide, x2 is equal to a liquid phase mol fraction of water, γ1 is equal to an activity coefficient for the hydrogen peroxide component, and γ2 is equal to an activity coefficient for the water component;
   e) sequentially varying values of the liquid phase mol factions for the hydrogen peroxide component (x1) and the water component (x2) from 0 to 1 under a condition specified by (Equation 3):

$$x1 + x2 = 1 \quad \text{(Equation 3)},$$

and thereby also sequentially varying the activity coefficients for the hydrogen peroxide component (γ1) and the water component (γ2);
   f) determining that condensation of hydrogen peroxide vapor occurs inside the decontamination target room if there exists a solution in which both (Equation 1) and (Equation 2) are true, or
   g) determining that condensation of hydrogen peroxide vapor does not occur inside the decontamination target room if there does not exist a solution with which both (Equation 1) and (Equation 2) are true.

2. The decontamination management method according to claim 1, wherein measuring the indoor humidity of the decontamination target room is accomplished using a computation model to account for the amount of water vapor generated as a consequence of the generation of hydrogen peroxide vapor from hydrogen peroxide solution, and the amount of water vapor generated due to the self-decomposition of the hydrogen peroxide vapor.

3. The decontamination management method according to claim 1, further comprising:
   repeatedly determining whether or not hydrogen peroxide condensation occurs throughout the decontamination process.

4. The decontamination management method according to claim 3, further comprising:
   computing the indoor humidity for each cycle of the indoor condensation determination using a computation model including, as a parameter thereof, the amount of water vapor generated due to the over-time self decomposition of hydrogen peroxide vapor in the decontamination target room.

5. The decontamination management method according to claim 1, wherein:
   if it is determined that hydrogen peroxide condensation occurs, using the substituted values used when both (Equation 1) and (Equation 2) held to calculate one or more of: the indoor hydrogen peroxide concentration after condensation occurs, the indoor hydrogen peroxide solution concentration, the amount of indoor hydrogen peroxide solution, or the indoor solution film thickness in the decontamination target room.

6. A decontamination management method, comprising:
   a) determining the hydrogen peroxide vapor pressure (PT'·y1') and water vapor pressure (PT'·y2') in a decontaminating gas feed passage using the temperature and humidity of the gas feed passage and a specified concentration of hydrogen peroxide;
   b) determining a saturated hydrogen peroxide vapor pressure (P01') if the hydrogen peroxide component existed alone at the temperature of the gas feed passage;
   c) determining a saturated water vapor pressure (P02') if the water component alone existed alone at the temperature of the gas feed passage;
   d) solving (Equation 1') and (Equation 2'), using the vapor pressures, (PT'·y1') and (PT'·y2'), and the saturated vapor pressures, (P01') and (P02'), obtained in steps (a) through (c)

$$PT' \cdot y1' = P01' \cdot x1 \cdot \gamma1 \quad \text{(Equation 1')},$$

$$PT' \cdot y2' = P02' \cdot x2 \cdot \gamma2 \quad \text{(Equation 2')},$$

wherein x1 is equal to a liquid phase mol fraction of hydrogen peroxide, x2 is equal to a liquid phase mol fraction of water, γ1 is equal to a activity coefficient for the hydrogen peroxide component, and γ2 is equal to a activity coefficient for the water component;
   e) sequentially varying values of the liquid phase mol fractions for the hydrogen peroxide component (x1) and the water component (x2) from 0 to 1 under a condition specified by (Equation 3'):

$$x1 + x2 = 1 \quad \text{(Equation 3')},$$

and thereby also sequentially varying the activity coefficients for the hydrogen peroxide component (γ1) and the water component (γ2);
   f) determining that condensation of hydrogen peroxide vapor occurs inside the decontaminating gas feed passage if there exists a solution in which both (Equation 1') and (Equation 2') are true, or g) determining that condensation of hydrogen peroxide vapor does not occur inside the decontaminating gas feed passage if there does not exist a solution with which both (Equation 1) and (Equation 2) are true.

7. A decontamination management method, wherein:
a) determining the hydrogen peroxide vapor pressure (PT·y1) and water vapor pressure (PT·y2) in the decontamination target room using the humidity of the decontamination target room and a specified concentration of hydrogen peroxide;
b) determining a saturated hydrogen peroxide vapor pressure (P01) if the hydrogen peroxide component existed alone at the surface temperature of an object in the decontamination target room;
c) determining a saturated water vapor pressure (P02) if the water component existed alone at the surface temperature of said object;
d) solving (Equation 1″) and (Equation 2″), using the vapor pressures, (PT″·y1″) and (PT″·y2″), and the saturated vapor pressures, (P01″) and (P02″), obtained in steps (a) through (c)

$$PT''\cdot y1''=P01''\cdot x1\cdot \gamma 1 \qquad \text{(Equation 1)},$$

$$PT''\cdot y2''=P02''\cdot x2\cdot \gamma 2 \qquad \text{(Equation 2)},$$

wherein x1 is equal to a liquid phase mol fraction of hydrogen peroxide, x2 is equal to a liquid phase mol fraction of water, γ1 is equal to an activity coefficient for the hydrogen peroxide component, and γ2 is equal to an activity coefficient for the water component;

e) sequentially varying values of the liquid phase mol fractions for the hydrogen peroxide component (x1) and the water component (x2) from 0 to 1 under a condition specified by (Equation 3″):

$$x1+x2=1 \qquad \text{(Equation 3'')},$$

and thereby also sequentially varying the activity coefficients for the hydrogen peroxide component (γ1) and the water component (γ2);

f) determining that condensation of hydrogen peroxide vapor occurs on the surface of said object in the decontamination target room if there exists a solution in which both (Equation 1″) and (Equation 2″) are true, or g) determining that condensation of hydrogen peroxide vapor does not occur on the surface of said object in the decontamination target room if there does not exist a solution with which both (Equation 1) and (Equation 2) are true.

\* \* \* \* \*

UNITED STATES PATENT AND TRADEMARK OFFICE
CERTIFICATE OF CORRECTION

PATENT NO. : 9,541,487 B2
APPLICATION NO. : 13/574477
DATED : January 10, 2017
INVENTOR(S) : Masanobu Saito et al.

Page 1 of 1

It is certified that error appears in the above-identified patent and that said Letters Patent is hereby corrected as shown below:

In the Claims

Column 19, Line 50, Claim 1, delete "factions" and insert -- fractions --

Signed and Sealed this
Fourth Day of April, 2017

Michelle K. Lee
*Director of the United States Patent and Trademark Office*